United States Patent
Mammadov et al.

(10) Patent No.: US 9,850,136 B2
(45) Date of Patent: *Dec. 26, 2017

(54) CATALYST FOR PURIFICATION OF $CO_2$ FROM CHLORINATED HYDROCARBONS

(71) Applicant: SAUDI BASIC INDUSTRIES CORPORATION, Riyadh (SA)

(72) Inventors: Aghaddin Kh. Mammadov, Houston, TX (US); Clark David Rea, Houston, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/028,992

(22) PCT Filed: Oct. 15, 2014

(86) PCT No.: PCT/US2014/060557
§ 371 (c)(1),
(2) Date: Apr. 13, 2016

(87) PCT Pub. No.: WO2015/057754
PCT Pub. Date: Apr. 23, 2015

(65) Prior Publication Data
US 2016/0264424 A1    Sep. 15, 2016

Related U.S. Application Data

(60) Provisional application No. 61/891,456, filed on Oct. 16, 2013.

(51) Int. Cl.
| | |
|---|---|
| C07C 29/151 | (2006.01) |
| C07C 29/04 | (2006.01) |
| B01D 53/86 | (2006.01) |
| B01D 53/96 | (2006.01) |
| B01J 37/02 | (2006.01) |
| B01J 23/26 | (2006.01) |
| B01D 53/70 | (2006.01) |
| C01B 31/20 | (2006.01) |
| B01J 38/12 | (2006.01) |
| B01J 21/04 | (2006.01) |
| B01J 23/92 | (2006.01) |
| C01B 32/50 | (2017.01) |

(52) U.S. Cl.
CPC .............. *C01B 31/20* (2013.01); *B01D 53/70* (2013.01); *B01D 53/8662* (2013.01); *B01D 53/8668* (2013.01); *B01D 53/96* (2013.01); *B01J 21/04* (2013.01); *B01J 23/26* (2013.01); *B01J 23/92* (2013.01); *B01J 37/0201* (2013.01); *B01J 38/12* (2013.01); *C01B 32/50* (2017.08); *C07C 29/04* (2013.01); *C07C 29/1518* (2013.01); *B01D 2255/2092* (2013.01); *B01D 2255/20784* (2013.01); *B01D 2256/22* (2013.01); *B01D 2257/2064* (2013.01); *B01D 2257/702* (2013.01); *B01D 2258/02* (2013.01); *Y02C 20/20* (2013.01); *Y02P 20/154* (2015.11); *Y02P 20/584* (2015.11)

(58) Field of Classification Search
CPC .......... B01J 23/26; C07C 29/04; C07C 31/20; C07C 29/1518; B01D 53/8662; B01D 53/96; B01D 38/12; B01D 53/8668; B01D 53/70; B01D 2255/20784; B01D 2255/2092
See application file for complete search history.

(56) References Cited

U.S. PATENT DOCUMENTS

| | | |
|---|---|---|
| 3,989,807 A | 11/1976 | Johnston |
| 4,330,513 A | 5/1982 | Hunter et al. |
| 4,488,890 A | 12/1984 | Foerg et al. |
| 5,457,268 A | 10/1995 | Greene et al. |
| 5,635,438 A | 6/1997 | Cowfer et al. |
| 5,653,949 A | 8/1997 | Chen et al. |
| 6,224,843 B1 | 5/2001 | Ahmed et al. |
| 7,381,243 B2 | 6/2008 | Alvarez, Jr. et al. |
| 2005/0069478 A1 | 3/2005 | Weckhuysen et al. |

(Continued)

FOREIGN PATENT DOCUMENTS

| | | |
|---|---|---|
| CN | 101069848 A | 11/2007 |
| CN | 101185796 A | 5/2008 |

(Continued)

OTHER PUBLICATIONS

Ferrandon; "Mixed Metal Oxide—Noble Metal Catalysts for Total Oxidation of Volatile Organic Compounds and Carbon Monoxide"; Dept. of Chem. Eng. & Tech.; Chem. Reaction Eng.; Royal Inst. of Tech.; 2001; 138 pages.
International Search Report for International Application No. PCT/US2014/060557; International Filing Date Oct. 15, 2014; dated Jan. 20, 2015; 5 pages.
Joon et al.; KR 2000042034 A; "Chromia/Zeolite Catalyst for Removing Chlorinated Volatile Organic Compounds and Method for Removing Them Using Same";Date fo Publication: Jul. 15, 2000; 1 Page, Abstract Only.
Miranda et al.; "Oxidation of trichloroethene over metal oxide catalysts: Kinetic studies and correlation with adsorption properties"; Chemosphere 66 (2007); pp. 1706-1715.
Paukshtis et al.; "Oxidative destruction of chlorinated hydrocarbons on Pt-containing fiber-glass catalysts"; Chemosphere, vol. 79; 2010; pp. 199-204.

(Continued)

*Primary Examiner* — Jafar Parsa
(74) *Attorney, Agent, or Firm* — Cantor Colburn LLP

(57) ABSTRACT

A process for the purification of $CO_2$ from chlorinated hydrocarbons and non-chlorinated hydrocarbons, comprising: contacting a $CO_2$ stream with a chromium oxide catalyst, wherein the stream comprises the $CO_2$, and impurities, wherein the impurities comprise the non-chlorinated hydrocarbons and the chlorinated hydrocarbons; forming a purified $CO_2$ stream by interacting the impurities with the chromium oxide catalyst to form additional $CO_2$ and chromium chloride; and regenerating the chromium oxide catalyst by contacting the chromium chloride with an oxygen containing gas stream.

20 Claims, 1 Drawing Sheet

(56) References Cited

U.S. PATENT DOCUMENTS

| | | |
|---|---|---|
| 2009/0324454 A1 | 12/2009 | Nakano et al. |
| 2011/0011263 A1 | 1/2011 | Hanke et al. |
| 2011/0044874 A1 | 2/2011 | Dang et al. |

FOREIGN PATENT DOCUMENTS

| | | |
|---|---|---|
| CN | 101249378 A | 8/2008 |
| EP | 0182649 A2 | 5/1986 |
| EP | 182649 B1 | 5/1986 |
| EP | 1084744 A1 | 3/2001 |
| EP | 1291070 A1 | 3/2003 |
| EP | 2505264 A1 | 10/2012 |
| WO | 9412432 A1 | 6/1994 |
| WO | 03057318 A1 | 7/2003 |
| WO | 2010101073 A1 | 9/2010 |
| WO | 2012006729 A1 | 1/2012 |
| WO | 2015057752 A1 | 4/2015 |

OTHER PUBLICATIONS

Rusu et al.; "Destruction of Volatile Organic Compounds by Catalytic Oxidation": Environmental Engineering and Management Journal; Dec. 2003; vol. 2; No. 4; pp. 273-302.

Szargan et al.; EP0612689 (A1); "Process and Catalyst for Purifying Carbon Dioxide", EP Filing Date Feb. 7, 1994; Date of Publication: Aug. 31, 1994; 1 Page; Abstract Only.

Van Der Averit Ir et al.; "Low temperature destruction of chlorinated hydrocarbons over lanthanide oxide-based catalysts"; Fuel Chemistry Division Reprints 2002; 47(2); 2 pages.

Van Der Avert et al.; "Low-Temperature Destructin of Chlorinated Hydrocarbons over Lanthanide Oxide Based Catalysts"; Angew. Chem. Int. Ed. 2002, 41, No. 24; pp. 4730-4732.

Written Opinion of the International Search Report for International Application No. PCT/US2014/060557; International Filing Date Oct. 15, 2014; dated Jan. 20, 2015; 6 pages.

KieBling et al., "Perovskite-type oxides-catalysts for the total oxidation of chlorinated hydrocarbons," Applied Catalysis B: Environmental; 1998, pp. 143-151, vol. 19.

CATALYST FOR PURIFICATION OF CO$_2$ FROM CHLORINATED HYDROCARBONS

CROSS REFERENCE TO RELATED APPLICATIONS

This application is a National Stage application of PCT/US2014/060557 filed Oct. 15, 2014, which claims the benefit of U.S. Provisional Application No. 61/891,456 filed Oct. 16, 2013, both of which are incorporated by reference in their entirety herein.

TECHNICAL FIELD

The present invention relates generally to the purification of carbon dioxide (CO$_2$), and for example, to the purification of carbon dioxide (CO$_2$) off-gas streams such as those produced in ethylene glycol plants.

BACKGROUND

CO$_2$ off-gas streams produced by ethylene glycol plants typically contain saturated and/or unsaturated chlorinated hydrocarbons. In order for the CO$_2$ off-gas to be used for the production of food grade products or for the production of methanol, urea, ethyl hexanol, or certain other applications, organic chlorides and hydrocarbons must be removed or substantially removed from the CO$_2$ to meet acceptable industrial limits. For food-grade CO$_2$, for example, hydrocarbons should be removed to below 5 ppmv (parts per million by volume).

Prior technologies for purification of such CO$_2$ off-gas streams have included attempts such as oxidation of saturated and unsaturated hydrocarbons alone on precious metal catalysts, for example palladium (Pd) or platinum (Pt) catalysts. Prior techniques have also included conversion of hydrocarbons in the CO$_2$ off-gas to CO$_2$ and H$_2$O followed by carbon dioxide vent to the atmosphere or further purification of a small stream of good grade CO$_2$ by adsorption on carbon.

Further techniques for the purification of CO$_2$ off-gas streams produced by ethylene glycol plants have included oxidation of saturated, unsaturated, and chlorinated hydrocarbons using a precious metal catalyst, for example platinum. Such methods have included the use of excess oxygen (i.e. a combustion process) for the oxidation of the saturated, unsaturated, and chlorinated hydrocarbons. Such methods have also included condensation of pure saturated water, removal of hydrogen chloride (HCl) on an adsorbent, and subsequent final removal of oxygen (O$_2$) by reaction with hydrogen (H$_2$) in the presence of a catalyst. Thereafter, chloride in the form of HCl is separated by absorption.

There remains a need, however, for more efficient and improved systems for the purification of carbon dioxide (CO$_2$) off-gas streams such as those produced in ethylene glycol plants.

BRIEF DESCRIPTION

Disclosed herein are improved systems and methods for purification of CO$_2$ off-gas streams produced by ethylene glycol plants.

In an embodiment: a process for the purification of CO$_2$ from chlorinated hydrocarbons and non-chlorinated hydrocarbons, comprising: contacting a CO$_2$ stream with a chromium oxide catalyst, wherein the stream comprises the CO$_2$, and impurities, wherein the impurities comprise the non-chlorinated hydrocarbons and the chlorinated hydrocarbons; forming a purified CO$_2$ stream by interacting the impurities with the chromium oxide catalyst to form additional CO$_2$ and chromium chloride; and regenerating the chromium oxide catalyst by contacting the chromium chloride with an oxygen containing gas stream.

In another embodiment: a process for the purification of CO$_2$ from chlorinated hydrocarbons and non-chlorinated hydrocarbons, comprising: contacting a CO$_2$ stream with a chromium oxide catalyst, wherein the CO$_2$ stream comprises the CO$_2$ and impurities, wherein the impurities comprise the non-chlorinated hydrocarbons and the chlorinated hydrocarbons; and forming a purified CO$_2$ stream by oxidizing the impurities in the CO$_2$ stream with catalyst oxygen to form additional CO$_2$ and converting the chlorine to chromium chloride; and regenerating the chromium oxide catalyst by contacting the chromium chloride with an oxygen containing gas stream; wherein no oxygen is added to the CO$_2$ stream before or during the contacting and the oxidizing.

In another embodiment: a process for the purification of CO$_2$ from chlorinated hydrocarbons and non-chlorinated hydrocarbons, comprising: contacting a CO$_2$ stream with a chromium oxide catalyst, wherein the CO$_2$ stream comprises the CO$_2$ and impurities, wherein the impurities comprise the non-chlorinated hydrocarbons and the chlorinated hydrocarbons; forming a purified CO$_2$ stream by oxidizing the impurities with catalyst oxygen to form additional CO$_2$ and converting the chlorine to chromium chloride; and regenerating the chromium oxide catalyst by contacting the chromium chloride with an oxygen containing gas stream; wherein the CO$_2$ stream comprises less than or equal to 0.3 ppmv of oxygen based on the total volume of the CO$_2$ stream.

In another embodiment: a process for the purification of CO$_2$ from chlorinated hydrocarbons and non-chlorinated hydrocarbons, comprising: reacting ethylene and oxygen with a chlorine containing catalyst to produce ethylene glycol, CO$_2$, and the chlorinated hydrocarbons; separating the ethylene glycol to form a CO$_2$ stream containing impurities, wherein the impurities comprise the non-chlorinated hydrocarbons and the chlorinated hydrocarbons; contacting the CO$_2$ stream with a chromium oxide catalyst; forming a purified CO$_2$ stream by oxidizing the impurities with catalyst oxygen to form additional CO$_2$ and converting the chlorine to chromium chloride; and regenerating the chromium oxide catalyst by contacting the chromium chloride with an oxygen containing gas stream.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

Figure 1:
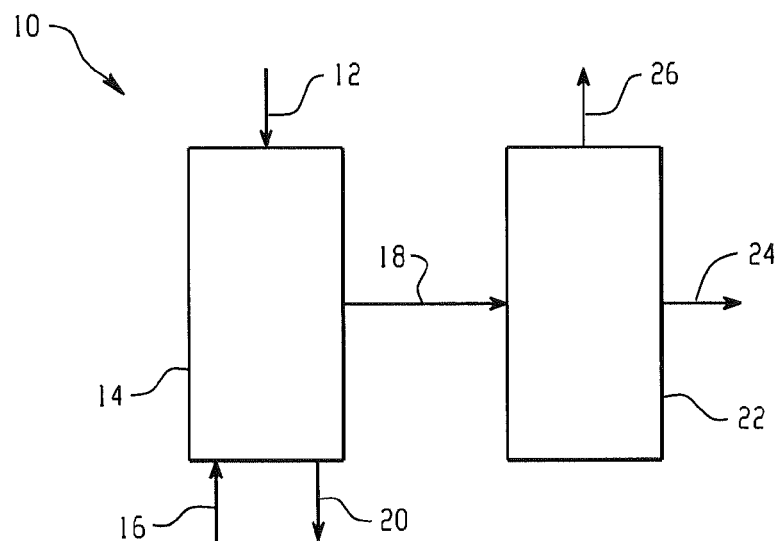
FIG. 1 is an illustration of a system and process for purification of a CO$_2$ off-gas stream.

Disclosed herein is a system and method for the purification of CO$_2$ off-gas streams containing impurities. Herein, "impurities" refers to one or more of saturated hydrocarbons, unsaturated hydrocarbons, and chlorinated hydrocarbons. The CO$_2$ stream can be a CO$_2$ stream comprising impurities, where the stream can comprise greater than or equal to 90 volume percent (vol %), preferably, greater than or equal to 99 vol % $CO_2$ based on the total volume of the stream. For example, the $CO_2$ stream can be a $CO_2$ off-gas stream from an ethylene glycol production plant. The method can allow for simultaneous oxidation of saturated, unsaturated, and/or chlorinated hydrocarbons, where the hydrocarbons can comprise 2 or more carbon atoms, preferably, 2 to 10 carbon atoms, more preferably, 2 to 4 carbon atoms. It is expected that purification of $CO_2$ in accordance with the method will be practical and efficient due to at least the use of a chromium oxide catalyst such that oxygen in the catalyst eliminates the need for a molecular oxygen feed to the reactor. The stoichiometric oxidation of the impurities by catalyst oxygen allows for purification of $CO_2$ due to the relatively low amount of the impurities relative to the oxygen capacity of the catalyst, where the $CO_2$ off-gas can comprise less than or equal to 200 ppmv, preferably, less than or equal to 100 ppmv, more preferably, less than or equal to 10 ppmv, still more preferably, 2 to 5 ppmv of impurities based on the total volume of $CO_2$ off-gas. For example, a typical composition of $CO_2$ off-gas from ethylene glycol plants is shown in Table 1.

TABLE 1*

| Composition | Amount |
|---|---|
| $O_2$ | 0.24 ppmv |
| Ar | (less than) 0.05 ppmv |
| $CH_4$ | 0.07 ppmv |
| $C_2H_4$ | 0.13 ppmv |
| $C_2H_6$ | (less than) 0.05 ppmv |
| $CO_2$ | 99.46 ppmv |
| EO (ethylene oxide) | (less than) 0.05 ppmv |
| $H_2O$ | Saturated at 93° C. |
| Methyl chloride | <0.1 ppmv |
| Vinyl chloride | <0.1 ppmv |
| Ethyl chloride | 2.5 ppmv |
| Allyl chloride | 0.1 ppmv |
| Ethylene dichloride | <0.1 ppmv |

*Units are volume percent on a dry basis

The system and method for the purification of $CO_2$ from streams containing organic chlorides can involve decomposition of organic chlorides in the presence of a chromium oxide catalyst such that organic substances are oxidized to $CO_2$, while chlorine is adsorbed by the catalyst with formation of the corresponding chromium chloride. In other words, the method allows for interaction of a $CO_2$ stream, containing impurities, with chromium oxide catalyst (e.g., in the absence of oxygen feed) and oxidizes the impurities to convert them into $CO_2$ and $H_2O$. Meanwhile any chlorine content of the hydrocarbons is transformed into chromium chloride. Accordingly, the $CO_2$ feed can comprise less than or equal to 0.3 ppmv, preferably, less than or equal to 0.001 ppmv of oxygen based on the total volume of the $CO_2$ feed and there can be no oxygen feed to the reactor or to a reaction zone during the purification. Accordingly, the contacting of the $CO_2$ stream with the catalyst can occur in the presence of less than or equal to 100 ppmv, preferably, less than or equal to 50 ppmv, more preferably, less than or equal to 0.3 ppmv, still more preferably, less than or equal to 0.001 ppmv of oxygen based on the total volume of the contacting gas.

During catalyst regeneration, the chromium chloride is oxidized back to chromium oxide with formation of molecular $Cl_2$. The molecular chlorine in the resultant regeneration gas can be absorbed by water. The method thus eliminates the need for a co-feed of oxygen with the $CO_2$ off-gas stream for the purification phase and further eliminates need for the subsequent removal of excess oxygen by, for example, reaction with hydrogen.

The process can thus include the use of a catalyst to substantially eliminate impurities in the $CO_2$ off-gas streams. For example, the impurities can be reduced to an amount of less than or equal to 0.01 ppmv, preferably, less than or equal to 0.001 ppmv based on the total amount of purified $CO_2$ off-gas. $CO_2$ off-gas streams often also include other components such as oxygen, argon, and/or water, where the oxygen in the $CO_2$ off-gas stream can be the only oxygen introduced to the catalyst during the purification reaction. Herein, oxygen for the process is provided by the catalyst, thereby eliminating the need for an additional molecular oxygen source during purification. This process thereby eliminates the need to remove excess oxygen from the purified $CO_2$, for example, in an oxidation step using hydrogen. The amount of $CO_2$ in the purified $CO_2$ stream can be greater than 99.5 vol %, preferably, greater than or equal to 99.99 vol % based on the total volume of the purified $CO_2$ stream.

For example, the impurities in the $CO_2$ off-gas feed streams to the reactor are oxidized into $CO_2$ and $H_2O$ using a chromium oxide catalyst, in the absence of an additional oxygen ($O_2$) source or oxygen feed, such that oxidative conversion of the hydrocarbons and/or other organic substances are transformed to $CO_2$ and $H_2O$. Meanwhile, the chlorine content in the hydrocarbons transforms to the chromium chloride form of the chromium oxide catalyst. Oxygen in the catalyst can be regenerated such that the chromium chloride form of the catalyst transforms to the initial state of the oxide form of the chromium oxide catalyst and molecular $Cl_2$ in the presence of an oxygen source such as air. Accordingly, the method allows for the implementation of a redox system that uses a chromium oxide catalyst or a mixture of a chromium oxide catalyst with a second metal oxide catalyst that uses a cycle alternating between reducing the oxide form to the chloride form of the catalyst and returning the chloride form back to oxide form during regeneration. The second metal can comprise a redox metal such as Mn, Sn, W, V, Mo, La, Ce, Pb, Mg, or a combination comprising one or more of the foregoing.

The catalyst can comprise an inert support, such as a silica, $Al_2O_3$, MgO, or the like. The catalyst can comprise 5 to 50 weight percent (wt %), preferably, 15 to 25 wt % of chromium oxide, based on the amount of chromium oxide and support. It is noted that for the present application, only the oxidation state of the chromium is significant in the purification of the $CO_2$ stream and the oxidation state of the support is not. Accordingly, the support can be in varied oxidations states, for example, the $Al_2O_3$ can comprise $\gamma$-$Al_2O_3$ and/or $\alpha$-$Al_2O_3$. The catalyst can therefore comprise spent Cr/$\alpha$-$Al_2O_3$ catalyst from an isobutylation reaction, where after about a year of activity in an isobutylation reaction, Cr/$\gamma$-$Al_2O_3$ catalyst is converted to Cr/$\alpha$-$Al_2O_3$ and no longer catalyzes said reaction.

The catalyst can be a formed catalyst and can be prepared by methods such as tableting, pelletizing, or extruding the support and optionally the chromium into a shape such as a sphere, a tablet, a pellet, an extrudate, or the like. If the chromium is not present during forming, then the chromium can be impregnated onto the support via, for example, an aqueous chromic acid. The formed catalyst can then be dried and/or calcined. The formed catalyst can be a sphere with an average diameter of, for example, 5 micrometers to 15 millimeters (mm). The formed catalyst can be an extrudate with a diameter of, for example, 0.5 to 10 mm with a length of, for example, 1 to 15 mm.

The catalyst can exhibit mild basic properties so as to promote the formation of $CO_2$ rather than carbonates as if the catalyst is too strong, then carbonates can form. As used herein, "mild basic properties" refers to a catalyst used in oxidation reactions that favors the production of $CO_2$ rather than carbonates. For example, the basic property of various elements can be determined by redox potential, where elements having redox potential within −1.180 to 0.774 can be considered the mild basic.

The $CO_2$, purified by the present method, can be used in applications where high purity $CO_2$ is required, for example for methanol synthesis where the concentration of the chlorinated hydrocarbons should be less than 0.01 ppmv based on the total volume of the $CO_2$ stream. The purified $CO_2$ stream can be first combined with syngas from a methane steam reforming source and then converted into methanol. The purified $CO_2$ can also be used for food grade applications.

Referring now to FIG. 1, a system 10 for purification of $CO_2$ off-gas streams such as that produced in an ethylene glycol plant is illustrated. As shown in FIG. 1, $CO_2$ off-gas feed stream 12 is fed to reactor 14. The $CO_2$ off-gas feed stream 12 can be fed to the reactor 14 without the addition of oxygen from another source. In other words, the $CO_2$ off-gas feed stream 12 can be added to the reactor as pure $CO_2$ off-gas feed and the reactor can be free of any additional oxygen stream added to the reactor 14 during the time when the $CO_2$ off-gas feed stream 12 is entering the reactor. The $CO_2$ feed stream can comprise less than or equal to 0.3 ppmv, preferably, less than or equal to 0.001 ppmv of oxygen based on the total volume of the $CO_2$ feed stream. The $CO_2$ off-gas feed stream 12 can have a composition similar to that shown in Table 1. Reactor 14 contains the chromium oxide catalyst. Reactor 14 can be, for example, a fixed bed reactor, a fluidized bed reactor, and the like.

The temperature in reactor 14 can be 400 to 500 degrees Celsius (° C.), preferably, 440 to 460° C., during the purification stages of processing. During the purification of $CO_2$, $CO_2$ off-gas feed stream 12 is contacted with the chromium oxide catalyst in reactor 14 for a time sufficient to remove the saturated hydrocarbons, unsaturated hydrocarbons, and chlorinated hydrocarbons from the $CO_2$ feed such that they are present in an amount of less than 0.01 ppmv based on the total volume of the $CO_2$ stream. The catalyst can be used on stream, before regenerating, for greater than or equal to 500 hours, preferably, 500 to 13,000 hours, more preferably, 4,500 to 9,000 hours. The catalyst can be used on stream, before regenerating, for 500 to 1,000 hours. The catalyst can be used on stream, before regenerating, for greater than or equal to 1 year. The contact time between the $CO_2$ off-gas stream 12 and the catalyst can be less than or equal to one minute, preferably, less than or equal to 30 seconds (sec), more preferably, less than or equal to 10 seconds, still more preferably, 1 to 3 seconds, or 2.4 to 3 seconds.

During processing, purification reactions occur for the chlorinated hydrocarbons. For example, chlorinated hydrocarbons in $CO_2$ off-gas stream 12 can react to form the corresponding saturated hydrocarbon and HCl. The HCl can then react with oxygen in the catalyst to form chromium chloride and $H_2O$. For purposes of illustration, using the impurity ethyl chloride ($C_2H_5Cl$), the following reactions 1-4 could occur:

$$C_2H_5Cl \rightarrow C_2H_4 + HCl \quad\quad 1$$

$$C_2H_4 + 4Cr_2O_3 \rightarrow 2CO_2 + 2H_2O + 2Cr_2O_3 \quad\quad 2$$

$$C_2H_4 + 6Cr_2O_3 \rightarrow 2CO_2 + 2H_2O + 12CrO \quad\quad 3$$

$$2CrO + 4HCl \rightarrow 2CrCl_2 + 2H_2O \quad\quad 4$$

Reactions similar to reactions 1-4 can also occur in reactor 14 for other chlorinated hydrocarbons present in $CO_2$ off-gas stream 12 to produce further $CO_2$, $H_2O$, and $CrCl_2$. After processing is initiated, reactions 1-4 can occur simultaneously. It is noted that in addition to reactions 1-4 occurring during purification, further reactions to convert various other saturated hydrocarbons and unsaturated hydrocarbons that may or may not be chlorinated to $CO_2$ and $H_2O$ can occur.

After contacting $CO_2$ off-gas stream 12 with the chromium oxide catalyst for a time sufficient to remove all or substantially all (i.e. such that the level of impurities is less than or equal to 0.01 ppmv based on the total volume of the $CO_2$ stream) of the saturated hydrocarbons, unsaturated hydrocarbons, and/or chlorinated hydrocarbons from the $CO_2$ off-gas, purified $CO_2$ and $H_2O$ are removed from reactor 14 as product stream 18. Product stream 18 can be sent to dewatering unit 22 for removal of water via stream 24 and purified product $CO_2$ stream 26 can be used in applications such as food grade products and methanol synthesis. The dewatering unit 22 can be, for example, a unit where the gas stream is passed through, for example caustic or calcium chloride or a silica gel, which then could be regenerated by drying.

As discussed above, purification can occur without an additional source of oxygen being added to the $CO_2$ off-gas feed stream. During purification, oxygen in the redox catalyst is consumed such that oxygen in the catalyst becomes depleted. Once the oxygen depletion reached a certain point, e.g., when that greater than or equal to 90%, preferably, greater than or equal to 99%, more preferably, 100% of the chromium oxide has been converted to chromium chloride regeneration of the catalyst can occur (e.g., with an oxygen source such as air or an oxygen stream) to transform the $CrCl_3$ back to molecular chloride and restore oxygen in the catalyst.

For example, regeneration of the oxygen in the catalyst can occur by the addition of oxygen (e.g., in stream 16) fed to reactor 14. During regeneration, flow of the $CO_2$ off-gas feed stream 12 to reactor 14 is ceased. Regeneration can be carried out in a reactor for a time sufficient to restore the oxygen content on the catalyst to a level that is sufficient to process the further $CO_2$ and provide an amount of oxygen for stoichiometric oxidation of the impurities. Likewise, the depleted catalyst can be removed from the reactor or from the reaction zone and regenerated in either a separate reactor and/or reaction zone. Depleted catalyst can be continuously replaced where fresh/regenerated catalyst can be continuously added such that $CO_2$ purification does not have to be stopped during the catalyst regeneration. The chromium oxide catalyst can be used for greater than or equal to 1 year without regeneration.

The oxygen can be restored such that greater than or equal to 90%, preferably, greater than or equal to 99%, more preferably, 100% of the chromium chloride is converted back to its chromium oxide form. Catalyst regeneration can take 1 to 60 hours, preferably, 10 to 24 hours.

The regeneration reaction 5 is exemplified as follows:

$$CrCl_2 + 1.5O_2 \rightarrow CrO_3 + Cl_2 \quad\quad (5)$$

The resultant chlorine ($Cl_2$) can be removed from reactor 14 via stream 20.

Figure 2:
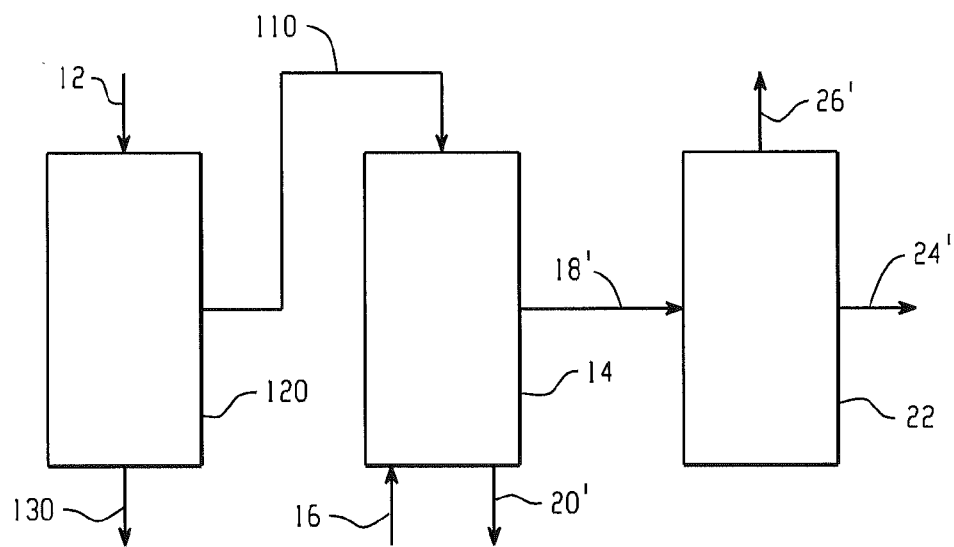
FIG. 2 is an illustration of a system and process for purification of a CO$_2$ off-gas stream.

As illustrated in FIG. 2, a dewatering unit can optionally be used upstream of the reactor 14. In particular, FIG. 2 shows a system 100 for the purification of $CO_2$ off-gas stream 12. As shown in FIG. 2, $CO_2$ off-gas feed stream 12 is fed to dewatering unit 120. Water in $CO_2$ off-gas stream 12 is removed in unit 120, for example, using an absorbent such as caustic, calcium chloride, or a silica gel such that water can be removed via stream 130. De-watered $CO_2$ off-gas feed stream 110 that can comprise less than or equal to 0.01 ppmv of water is then fed to reactor 14 for purification of $CO_2$ as discussed hereinabove with regard to reactor 14. $CO_2$ and $H_2O$ are removed from unit 14 via product stream 18' and fed to dewatering unit 22. Dewatering unit 22 separates $H_2O$ via stream 24' and product $CO_2$ stream 26'.

As detailed above, it is expected that purification of $CO_2$ in accordance with the present system and method provides a practical solution for the purification of $CO_2$, and for example to the purification of $CO_2$ off-gas streams from ethylene glycol plants. Oxygen in the redox catalyst allows purification to occur of pure $CO_2$ off-gas without the need for an additional source of oxygen fed to the reactor during the purification phase. This further allows the elimination of the addition of hydrogen to remove excess oxygen from the $CO_2$. It is believed that the stoichiometric oxidation of the impurities by catalyst oxygen allows purification of $CO_2$ due to the very low ratio of the amount of impurities to the oxygen capacity of the catalyst.

Example: A $CO_2$ off-gas stream containing chlorinated hydrocarbons, was fed to a reactor containing 1.5 grams (g) of a CATOFIN catalyst. The temperature in the reactor was 500° C., and the pressure was atmospheric. The $CO_2$ off-gas stream was contacted with the catalyst. The flow rate of the $CO_2$ off-gas stream was 50 cubic centimeters per minute (cc/min). At this flow rate, after interaction of the $CO_2$ off-gas stream with the catalyst, all of the chlorinated impurities were removed. Testing of the product stream in the gas chromatograph (GC) after one month of purification showed that the product stream was still free of chlorinated contaminants.

Set forth below are various embodiments of the present method of purifying a $CO_2$ stream containing impurities.

Embodiment 1: a process for the purification of $CO_2$ from chlorinated hydrocarbons and non-chlorinated hydrocarbons, comprising: contacting a $CO_2$ stream with a chromium oxide catalyst, wherein the stream comprises the $CO_2$, and impurities, wherein the impurities comprise the non-chlorinated hydrocarbons and the chlorinated hydrocarbons; forming a purified $CO_2$ stream by interacting the impurities with the chromium oxide catalyst to form additional $CO_2$ and chromium chloride; and regenerating the chromium oxide catalyst by contacting the chromium chloride with an oxygen containing gas stream.

Embodiment 2: a process for the purification of $CO_2$ from chlorinated hydrocarbons and non-chlorinated hydrocarbons, comprising: contacting a $CO_2$ stream with a chromium oxide catalyst, wherein the $CO_2$ stream comprises the $CO_2$ and impurities, wherein the impurities comprise the non-chlorinated hydrocarbons and the chlorinated hydrocarbons; and forming a purified $CO_2$ stream by oxidizing the impurities in the $CO_2$ stream with catalyst oxygen to form additional $CO_2$ and converting the chlorine to chromium chloride; and regenerating the chromium oxide catalyst by contacting the chromium chloride with an oxygen containing gas stream; wherein no oxygen is added to the $CO_2$ stream before or during the contacting and the oxidizing.

Embodiment 3: a process for the purification of $CO_2$ from chlorinated hydrocarbons and non-chlorinated hydrocarbons, comprising: contacting a $CO_2$ stream with a chromium oxide catalyst, wherein the $CO_2$ stream comprises the $CO_2$ and impurities, wherein the impurities comprise the non-chlorinated hydrocarbons and the chlorinated hydrocarbons; forming a purified $CO_2$ stream by oxidizing the impurities with catalyst oxygen to form additional $CO_2$ and converting the chlorine to chromium chloride; and regenerating the chromium oxide catalyst by contacting the chromium chloride with an oxygen containing gas stream; wherein the $CO_2$ stream comprises less than or equal to 0.3 ppmv of oxygen based on the total volume of the $CO_2$ stream.

Embodiment 4: a process for the purification of $CO_2$ from chlorinated hydrocarbons and non-chlorinated hydrocarbons, comprising: reacting ethylene and oxygen with a chlorine containing catalyst to produce ethylene glycol, $CO_2$, and the chlorinated hydrocarbons; separating the ethylene glycol to form a $CO_2$ stream containing impurities, wherein the impurities comprise the non-chlorinated hydrocarbons and the chlorinated hydrocarbons; contacting the $CO_2$ stream with a chromium oxide catalyst; forming a purified $CO_2$ stream by oxidizing the impurities with catalyst oxygen to form additional $CO_2$ and converting the chlorine to chromium chloride; and regenerating the chromium oxide catalyst by contacting the chromium chloride with an oxygen containing gas stream.

Embodiment 5: the process of Embodiment 4, wherein the $CO_2$ stream comprises less than or equal to 0.3 ppmv of oxygen.

Embodiment 6: the process of Embodiment 4 or Embodiment 5, wherein no oxygen ($O_2$) is added to the $CO_2$ stream before or during the contacting and the forming.

Embodiment 7: the process any of Embodiments 1-6, wherein the contacting occurs in the presence of less than or equal to 100, preferably, less than or equal to 50 ppmv, more preferably, less than or equal to 0.3 ppmv, still more preferably, less than or equal to 0.001 ppmv of oxygen ($O_2$) based on the total volume of the contacting gas.

Embodiment 8: The process of any of Embodiments 1-7, wherein the regenerating produces molecular chlorine and wherein the process further comprises absorbing the molecular chlorine with water.

Embodiment 9: the process of any of Embodiments 1-8, wherein the contacting is performed at a temperature of 400 to 500° C.

Embodiment 10: the process of any of Embodiments 1-9, wherein the regenerating is performed for a time of less than or equal to 60 hours, preferably, 1 to 60 hours, more preferably, 10 to 24 hours.

Embodiment 11: the process of any of Embodiments 1-10, wherein the contacting is at a temperature of 440 to 460° C.

Embodiment 12: the process of any of Embodiments 1-11, wherein the contact time of the $CO_2$ stream with the catalyst is 2.4 to 3 sec.

Embodiment 13: the process of any of Embodiments 1-12, wherein the purified $CO_2$ stream comprises less than or equal to 0.01 ppmv of chlorinated hydrocarbons.

Embodiment 14: the process of any of Embodiments 1-13, wherein the contacting is performed for a time of greater than or equal to 170 hours.

Embodiment 15: the process of any of Embodiments 1-14, wherein the contacting is performed under conditions that oxygen is not added to the $CO_2$ stream and the $CO_2$ stream was not an oxygen diluted $CO_2$ stream.

Embodiment 16: the process of any of Embodiments 1-15, wherein catalyst further comprises a second metal oxide, wherein the metal comprises Mn, Sn, W, V, Mo, La, Ce, Pb, Mg, or a combination comprising one or more of the foregoing.

Embodiment 17: the process of any of Embodiments 1-16, wherein the catalyst comprises an inert support.

Embodiment 18: the process of Embodiment 16, wherein the inert support comprises a silica, $Al_2O_3$, MgO, or a combination comprising one or more of the foregoing.

Embodiment 19: the process of any of Embodiments 17-18, wherein the catalyst comprises 5 to 50 wt %, preferably, 15 to 25 wt % of chromium oxide, based on the amount of chromium oxide and the inert support.

Embodiment 20: the process of any of Embodiments 18-19, wherein the inert support comprises the $Al_2O_3$ and wherein the $Al_2O_3$ comprises $Cr/\gamma\text{-}Al_2O_3$ and/or $Cr/\alpha\text{-}Al_2O_3$.

Embodiment 21: the process of Embodiment 20, wherein $\alpha\text{-}Al_2O_3$ comprises spent $\alpha\text{-}Al_2O_3$ catalyst from an isobutylation reaction.

Embodiment 22: the process of any of Embodiments 1-21, wherein the catalyst is a formed catalyst.

Embodiment 23: the process of any of Embodiments 1-22, wherein the catalyst exhibits mild basic properties.

Embodiment 24: the process of any of Embodiments 1-23, wherein the purified $CO_2$ stream is converted into methanol.

Embodiment 25: the process of any of Embodiments 1-23, wherein the purified $CO_2$ stream is combined with syngas from a methane stream reforming source and converted into methanol.

Embodiment 26: the process of any of Embodiments 1-25, wherein the $CO_2$ stream comprises greater than or equal to 90 vol %, preferably, greater than or equal to 99 vol % $CO_2$, based on the total volume of the $CO_2$ stream.

Embodiment 27: the process of any of Embodiments 1-26, wherein the $CO_2$ stream comprises less than or equal to 200 ppmv, preferably, less than or equal to 100 ppmv, more preferably, less than or equal to 10 ppmv, still more preferably, 2 to 5 ppmv of impurities based on the total volume of the $CO_2$ stream.

Embodiment 28: the process of any of Embodiments 1-27, wherein the purified $CO_2$ stream comprises greater than 99.5 vol %, preferably, greater than or equal to 99.99 vol % based on the total volume of the purified $CO_2$ stream.

Embodiment 29: the process of any of Embodiments 1-28, wherein the regenerating comprises ceasing a flow of the $CO_2$ stream and introducing an oxygen stream to the chromium oxide catalyst.

Embodiment 30: the process of any of Embodiments 1-28, wherein the regenerating comprises removing chromium chloride from a first reaction zone and introducing oxygen to the chromium chloride in a second reaction zone to form regenerated chromium oxide and introducing the regenerated chromium oxide to the first reaction zone.

Embodiment 31: the process of Embodiment 30, wherein the removing and the introducing of the regenerated chromium oxide is continuous.

Embodiment 32: the process of any of Embodiments 30-31, wherein the first reaction zone is a first reactor and the second reaction zone is a second reactor.

Embodiment 33: the process of any of Embodiments 30-31, wherein the first reaction zone and the second reaction zone are located in a single reactor.

Embodiment 34: the process of any of Embodiments 1-33, wherein the chromium oxide catalyst is used for greater than or equal to 500 hours, preferably, greater than or equal to 1 year before the regenerating.

Embodiment 35: the process of any of Embodiments 1-34, wherein the regenerating converts greater than or equal to 90%, preferably, greater than or equal to 99%, more preferably, 100% of the chromium chloride back to its chromium oxide form.

Embodiment 37: the process of any of Embodiments 1-36, further comprising dewatering the $CO_2$ stream prior to contacting.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, preferably, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. This application claims priority to U.S. Patent Application 61/891,456 both filed Oct. 16, 2013, which is incorporated herein by reference in its entirety.

While particular embodiments have been described, alternatives, modifications, variations, improvements, and substantial equivalents that are or may be presently unforeseen may arise to Applicants or others skilled in the art. Accordingly, the appended claims as filed and as they may be amended are intended to embrace all such alternatives, modifications variations, improvements, and substantial equivalents.

Disclosure of a narrower range or more specific group in addition to a broader range is not a disclaimer of the broader range or larger group.

We claim:

1. A process for the purification of $CO_2$ from chlorinated hydrocarbons and non-chlorinated hydrocarbons, comprising:

contacting a $CO_2$ stream with a chromium oxide catalyst, wherein the stream comprises the $CO_2$, and impurities, wherein the impurities comprise the non-chlorinated hydrocarbons and the chlorinated hydrocarbons;

forming a purified $CO_2$ stream by interacting the impurities with the chromium oxide catalyst to form additional $CO_2$ and chromium chloride; and regenerating the chromium oxide catalyst by contacting the chromium chloride with an oxygen containing gas stream.

2. A process for the purification of $CO_2$ from chlorinated hydrocarbons and non-chlorinated hydrocarbons, comprising:

contacting a $CO_2$ stream with a chromium oxide catalyst, wherein the $CO_2$ stream comprises the $CO_2$ and impurities, wherein the impurities comprise the non-chlorinated hydrocarbons and the chlorinated hydrocarbons; and forming a purified $CO_2$ stream by oxidizing the impurities in the $CO_2$ stream with catalyst oxygen to form additional $CO_2$ and converting the chlorine to chromium chloride; and regenerating the chromium oxide catalyst by contacting the chromium chloride with an oxygen containing gas stream;

wherein no oxygen is added to the $CO_2$ stream before or during the contacting and the oxidizing.

3. A process for the purification of $CO_2$ from chlorinated hydrocarbons and non-chlorinated hydrocarbons, comprising:

contacting a $CO_2$ stream with a chromium oxide catalyst, wherein the $CO_2$ stream comprises the $CO_2$ and impurities, wherein the impurities comprise the non-chlorinated hydrocarbons and the chlorinated hydrocarbons;

forming a purified $CO_2$ stream by oxidizing the impurities with catalyst oxygen to form additional $CO_2$ and converting the chlorine to chromium chloride; and regenerating the chromium oxide catalyst by contacting the chromium chloride with an oxygen containing gas stream;

wherein the $CO_2$ stream comprises less than or equal to 0.3 ppmv of oxygen based on the total volume of the $CO_2$ stream.

4. The process of claim 1, further comprising:

prior to the contacting, reacting ethylene and oxygen with a chlorine containing catalyst to produce ethylene glycol, $CO_2$, and the chlorinated hydrocarbons; and separating the ethylene glycol to form the $CO_2$ stream;

wherein the forming comprising forming the purified $CO_2$ stream by oxidizing the impurities with catalyst oxygen to form the additional $CO_2$ and converting the chlorine to chromium chloride.

5. The process of claim 4, wherein the $CO_2$ stream comprises less than or equal to 0.3 ppmv of oxygen.

6. The process of claim 4, wherein no oxygen is added to the $CO_2$ stream before or during the contacting and the forming.

7. The process of claim 1, wherein the regenerating produces molecular chlorine and wherein the process further comprises absorbing the molecular chlorine with water.

8. The process of claim 1, wherein the regenerating is performed for a time of less than or equal to 60 hours.

9. The process of claim 1, wherein the contacting is performed at a temperature of 400 to 500° C.

10. The process of claim 1, wherein the contact time of the $CO_2$ stream with the catalyst is 2.4 to 3 sec.

11. The process of claim 1, wherein the purified $CO_2$ stream comprises less than or equal to 0.01 ppmv of chlorinated hydrocarbons.

12. The process of claim 1, wherein the contacting is performed for a time of greater than or equal to 170 hours.

13. The process of claim 1, wherein the contacting is performed under conditions that oxygen is not added to the $CO_2$ stream and the $CO_2$ stream was not an oxygen diluted $CO_2$ stream.

14. The process of claim 1, wherein the catalyst further comprises a second metal oxide comprising a metal, wherein the metal comprises Mn, Sn, W, V, Mo, La, Ce, Pb, Mg, or a combination comprising one or more of the foregoing.

15. The process of claim 1, wherein the purified $CO_2$ stream is converted into methanol.

16. The process of claim 1, wherein the purified $CO_2$ stream is combined with syngas from a methane stream reforming source and converted into methanol.

17. The process of claim 1, wherein the chromium oxide catalyst comprises $Cr/\gamma$-$Al_2O_3$ and/or $Cr/\alpha$-$Al_2O_3$.

18. The process of claim 17, wherein the chromium oxide catalyst comprises $Cr/\alpha$-$Al_2O_3$ from an isobutylation reaction.

19. The process of claim 1, wherein the $CO_2$ stream comprises greater than or equal to 90 vol % $CO_2$ based on the total volume of the $CO_2$ stream.

20. The process of claim 1, wherein the $CO_2$ stream comprises less than or equal to 200 ppmv of impurities based on the total volume of the $CO_2$ stream.

* * * * *